(12) United States Patent
Kuonanoja

(10) Patent No.: US 12,383,137 B2
(45) Date of Patent: Aug. 12, 2025

(54) ANTENNA IN A WEARABLE DEVICE

(71) Applicant: Oura Health Oy, Oulu (FI)

(72) Inventor: Reetta Kuonanoja, Oulu (FI)

(73) Assignee: Oura Health Oy, Oulu (FI)

( * ) Notice: Subject to any disclaimer, the term of this patent is extended or adjusted under 35 U.S.C. 154(b) by 240 days.

(21) Appl. No.: 18/173,691

(22) Filed: Feb. 23, 2023

(65) Prior Publication Data

US 2023/0277056 A1    Sep. 7, 2023

Related U.S. Application Data

(60) Provisional application No. 63/316,040, filed on Mar. 3, 2022.

(51) Int. Cl.
| | |
|---|---|
| *A61B 5/00* | (2006.01) |
| *A44C 9/00* | (2006.01) |
| *H01Q 1/27* | (2006.01) |
| *H01Q 1/48* | (2006.01) |

(52) U.S. Cl.
CPC .......... *A61B 5/0002* (2013.01); *A44C 9/0053* (2013.01); *A61B 5/6826* (2013.01); *H01Q 1/273* (2013.01); *H01Q 1/48* (2013.01); *A61B 2562/166* (2013.01)

(58) Field of Classification Search
CPC ....... A61B 5/0002; A61B 5/6826; A61B 5/01; A61B 5/02427; A61B 5/02438; A61B 5/4812; A61B 2562/16; A44C 9/0053; H01Q 1/273; H01Q 1/48; H01Q 1/2291; H01Q 9/42
See application file for complete search history.

(56) References Cited

U.S. PATENT DOCUMENTS

| | | | | |
|---|---|---|---|---|
| 10,834,535 | B2 * | 11/2020 | Laakkonen | A61B 5/06 |
| 11,349,191 | B1 * | 5/2022 | Napoles | H01M 10/4257 |
| 11,829,831 | B1 * | 11/2023 | Ershov | G06K 19/07762 |
| 2016/0218416 | A1 * | 7/2016 | Van Wonterghem | H01Q 1/243 |
| 2017/0207519 | A1 * | 7/2017 | Tzanidis | H01Q 1/38 |
| 2018/0103902 | A1 * | 4/2018 | Haverinen | G06F 1/163 |
| 2019/0181544 | A1 * | 6/2019 | Kim | H01Q 1/38 |
| 2019/0190128 | A1 * | 6/2019 | Shaker | H01Q 1/362 |
| 2019/0393590 | A1 * | 12/2019 | Choi | H01Q 9/0414 |
| 2021/0265054 | A1 * | 8/2021 | Kosman | G06F 1/163 |
| 2021/0389829 | A1 * | 12/2021 | Erivantcev | H02J 7/342 |
| 2022/0019993 | A1 * | 1/2022 | Rezayee | H04B 5/26 |
| 2022/0069439 | A1 * | 3/2022 | Kuo | H04B 1/38 |

(Continued)

FOREIGN PATENT DOCUMENTS

| | | | | |
|---|---|---|---|---|
| CN | 112448147 A | * | 3/2021 | H01Q 1/22 |
| CN | 112841831 A | * | 5/2021 | A44C 9/0053 |

(Continued)

*Primary Examiner* — Seokjin Kim
(74) *Attorney, Agent, or Firm* — Holland & Hart LLP

(57) ABSTRACT

A wearable device is described. The wearable device may include an antenna ground plane disposed along a first circumferential portion of the wearable device. The wearable device may also include an antenna that is disposed along the second circumferential portion and that is separated from the antenna ground plane by a spacing. An interconnect portion of the antenna, which may couple a radiator of the antenna with an input of a communication component, may be coupled with the antenna ground plane.

14 Claims, 5 Drawing Sheets

(56) References Cited

U.S. PATENT DOCUMENTS

| | | | | |
|---|---|---|---|---|
| 2022/0084974 | A1* | 3/2022 | Akejima | H01L 21/56 |
| 2022/0296111 | A1* | 9/2022 | Leabman | A61B 5/681 |
| 2023/0037029 | A1* | 2/2023 | Samardzija | H01Q 1/085 |
| 2023/0043018 | A1* | 2/2023 | Wai | H01Q 9/265 |
| 2023/0134920 | A1* | 5/2023 | Su | H02J 50/23 |
| | | | | 320/107 |
| 2023/0225671 | A1* | 7/2023 | Kosman | A61B 5/6826 |
| | | | | 600/300 |
| 2023/0229205 | A1* | 7/2023 | Deschamps | A61B 5/7405 |
| | | | | 381/345 |
| 2024/0164716 | A1* | 5/2024 | Mars | G01K 1/143 |
| 2024/0281095 | A1* | 8/2024 | Hunt | G06F 3/0488 |

FOREIGN PATENT DOCUMENTS

| | | | | | |
|---|---|---|---|---|---|
| CN | 213144151 | U | * | 5/2021 | |
| CN | 112909556 | A | * | 6/2021 | H01Q 1/273 |
| CN | 113300086 | A | * | 8/2021 | H01Q 1/273 |
| CN | 115250126 | A | * | 10/2022 | G08C 17/02 |
| DE | 102021107263 | A1 | * | 9/2022 | A44C 25/00 |
| EP | 3528176 | B1 | * | 12/2022 | G06K 19/077 |
| WO | WO-2022175005 | A1 | * | 8/2022 | A44C 9/0053 |

\* cited by examiner

ANTENNA IN A WEARABLE DEVICE

CROSS REFERENCES

The present Application for Patent claims priority to U.S. Provisional Patent Application No. 63/316,040 by Kuonanoja et al., entitled "ANTENNA IN A WEARABLE DEVICE," filed Mar. 3, 2022, which is assigned to the assignee hereof and which is expressly incorporated by reference herein.

FIELD OF TECHNOLOGY

The following relates to wearable devices and data processing, including designs for an antenna in a wearable device.

BACKGROUND

Some wearable devices may be configured to collect data, such as physiological data, from users using sensors. A wearable device may use an antenna to communicate data, or other information, to another device, such as a user device. Some antenna designs for wearable devices may have limitations on throughput, bandwidth range, transmission distance, or the like due to physical limitations of the size of the antenna, limitations on power due to the size of the on-board battery, or a combination of these and other limitations. As such, improved designs for an antenna in a wearable device may be desired.

DETAILED DESCRIPTION

A wearable device, such as a wearable ring device, may use an antenna to wirelessly communicate with another device, such as a user device. For example, the wearable device may use the antenna to exchange information, such as physiological data collected by the wearable device, with the user device. In some wearable devices, the antenna may be a trace antenna that is formed by conductive traces on a circuit board that is disposed along a circumferential portion of the wearable device. Together with an antenna ground plane (which may be the ground plane of the circuit board and/or a metal chassis of the wearable device), the trace antenna may generate an electromagnetic field that the wearable device uses for wireless communications. But performance of an antenna (e.g., the antenna range, the antenna efficiency, the antenna bandwidth) may be a function of the size of the antenna—which may be limited by the size of the wearable device—as well as the distance between the trace antenna and the ground plane—which may be limited by the placement of the trace antenna on the circuit board. So, use of a trace antenna may negatively impact the communication ability of a wearable device.

According to the designs described herein, the communication ability of a wearable device may be improved, relative to other techniques, by using a separate (e.g., planar) antenna that is disposed along a circumferential portion of a wearable device that is opposite the circumferential portion along which the antenna ground plane is disposed. Disposition of the antenna along the opposite circumferential portion may allow for a larger antenna relative to other techniques and may increase the size of the antenna relative to other techniques, both aspects of which may increase the performance (e.g., range, efficiency, bandwidth) of the antenna.

Placement of the antenna along a circumferential portion (e.g., the outer circumferential portion) of the wearable device may increase exposure of the antenna to electrostatic discharge (e.g., during the manufacturing process). If the electrostatic discharge on the antenna flows into a communication component of the wearable device, the communication component may be damaged. According to the designs described herein, damage from electrostatic shock may be reduced by coupling an interconnect portion of the antenna—which may be coupled with the input of the communication component—with a ground plane of the wearable device so that charge on the antenna is conducted to the ground plane instead of the communication component.

Aspects of the disclosure are initially described in the context of systems supporting physiological data collection from users via wearable devices. Additional features of the disclosure are described in the context of a wearable device. Aspects of the disclosure are further illustrated by and described with reference to apparatus diagrams, system diagrams, and flowcharts that relate to antenna in a wearable device.

Figure 1:
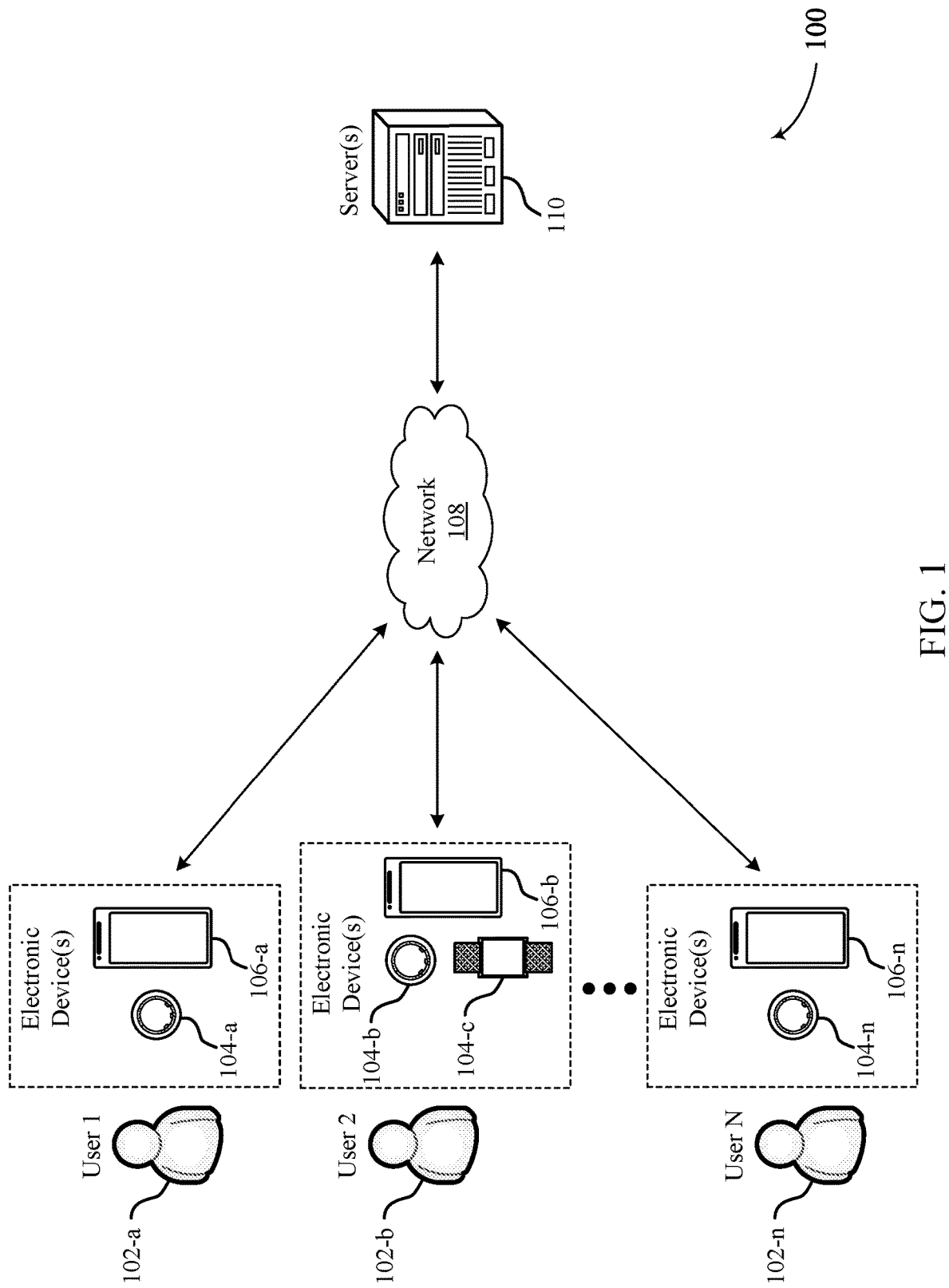
FIG. 1 illustrates an example of a system that supports antenna designs in a wearable device in accordance with aspects of the present disclosure.

FIG. 1 illustrates an example of a system 100 that supports antenna in a wearable device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "wearable device 104," "wearable device 104," and like terms, may be used interchangeably, unless noted otherwise herein. However, the use of the term "wearable device 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., wearable device 104-*a*) and a user device 106-*a* that may operate as described herein. In this example, the user device 106-*a* associated with user 102-*a* may process/store physiological parameters measured by the wearable device 104-*a*. Comparatively, a second user 102-*b* (User 2) may be associated with a wearable device 104-*b*, a watch wearable device 104-*c* (e.g., watch 104-*c*), and a user device 106-*b*, where the user device 106-*b* associated with user 102-*b* may process/store physiological parameters measured by the wearable device 104-*b* and/or the watch 104-*c*. Moreover, an nth user 102-*n* (User N) may be associated with an arrangement of electronic devices described herein (e.g., wearable device 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a wearable device 104 may utilize one or more LEDs (e.g., red LEDs, green LEDs) that emit light on the palm-side of a user's finger to collect physiological data based on arterial blood flow within the user's finger. In some implementations, the wearable device 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the wearable device 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a wearable device 104 has been found to exhibit superior performance as compared to wearable devices worn on the wrist, as the wearable device 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the wearable device 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-a may be associated with a wearable device 104-a (e.g., wearable device 104-a) and a user device 106-a. In this example, the wearable device 104-a may collect physiological data associated with the user 102-a, including temperature, heart rate, HRV, respiratory rate, and the like. In some aspects, data collected by the wearable device 104-a may be input to a machine learning classifier, where the machine learning classifier is configured to determine periods of time during which the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle and that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

To facilitate communications with a user device 106, a wearable device 104 may include an antenna. According to the techniques described herein, the antenna may be disposed along the circumferential portion of the wearable device 104 that is opposite the circumferential portion along which an antenna ground plane is disposed. For example, if the antenna ground plane is disposed along the inner circumferential portion of the wearable device 104, the antenna may be disposed along an outer circumferential portion of the wearable device 104. Such a design may allow the antenna to be larger in size, and farther from the antenna ground plane, compared to other designs, which in turn may improve the performance (e.g., range, efficiency, bandwidth) of the antenna relative to other designs. Increased antenna performance may allow the wearable device 104 to communicate with the user device 106 at greater distances, which may improve user experience.

To reduce damage from electrostatic discharge (the risk of which may be increased by placing the antenna along a circumferential portion of the wearable device), an interconnect portion of the antenna may be coupled with the antenna ground plane.

Although described with reference to circumferential portions of a curved wearable device, such as a ring, the designs described herein may be used in wearable devices that have linear or flat portions in addition to, or instead of, circumferential portions. For example, a wearable device (e.g., a watch) may have a flat outer portion and/or a flat inner portion that is configured to interface with the user's skin. In such a wearable device, the antenna ground plane may be disposed along the inner portion of the wearable device and the antenna may be disposed along the outer circumferential portion of the wearable device (or vice versa).

It should be appreciated by a person skilled in the art that one or more aspects of the disclosure may be implemented in a system 100 to additionally or alternatively solve other problems than those described herein. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
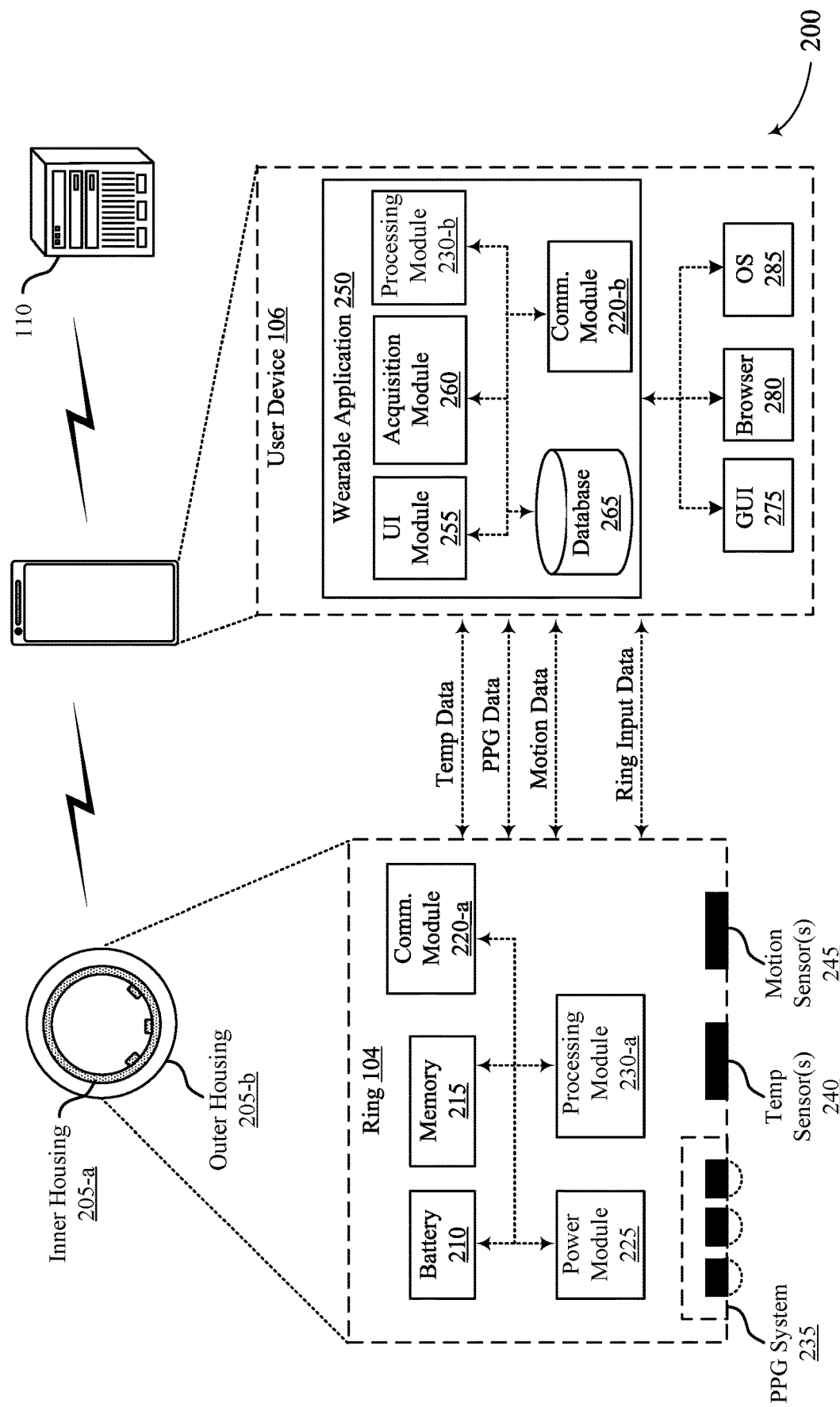
FIG. 2 illustrates an example of a system that supports antenna designs in a wearable device in accordance with aspects of the present disclosure.

FIG. 2 illustrates an example of a system 200 that supports antenna in a wearable device in accordance with aspects of the present disclosure. The system 200 may implement, or be implemented by, system 100. In particular, system 200 illustrates an example of a wearable device 104 (e.g., wearable device 104), a user device 106, and a server 110, as described with reference to FIG. 1.

In some aspects, the wearable device 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the wearable device 104. For example, the wearable device 104 may be in wireless and/or wired communication with the user device 106. In some implementations, the wearable device 104 may send measured and processed data (e.g., temperature data, photoplethysmogram (PPG) data, motion/accelerometer data, ring input data, and the like) to the user device 106. The user device 106 may also send data to the wearable device 104, such as wearable device 104 firmware/configuration updates. The user device 106 may process data. In some implementations, the user device 106 may transmit data to the server 110 for processing and/or storage.

The wearable device 104 may include a housing 205, which may include an inner housing 205-a and an outer housing 205-b. In some aspects, the housing 205 of the wearable device 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the wearable device 104, and generate signals associated with the respective sensors. In some aspects, each of the components/modules of the wearable device 104 may be communicatively coupled to one another via wired or wireless connections. Moreover, the wearable device 104 may include additional and/or alternative sensors or other components that are configured to collect physiological data from the user, including light sensors (e.g., LEDs), oximeters, and the like.

The wearable device 104 shown and described with reference to FIG. 2 is provided solely for illustrative purposes. As such, the wearable device 104 may include additional or alternative components as those illustrated in FIG. 2. Other rings 104 that provide functionality described herein may be fabricated. For example, rings 104 with fewer components (e.g., sensors) may be fabricated. In a specific example, a wearable device 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a wearable device 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the wearable device 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The wearable device 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the wearable device 104 in a variety of ways. In some implementations, one substrate that includes device electronics may be mounted along the bottom of the wearable device 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the wearable device 104 (e.g., on another substrate).

The various components/modules of the wearable device 104 represent functionality (e.g., circuits and other components) that may be included in the wearable device 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the wearable device 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the wearable device 104 described herein are only example device electronics. As such, the types of electronic components used to implement the device electronics may vary based on design considerations.

The functions attributed to the modules of the wearable device 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the wearable device 104 may include one or more processors (e.g., processing units), microcontrollers, digital signal processors, systems on a chip (SOCs), and/or other processing devices. The processing module 230-*a* communicates with the modules included in the wearable device 104. For example, the processing module 230-*a* may transmit/receive data to/from the modules and other components of the wearable device 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the wearable device 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or wearable device 104 configuration settings). The processing module 230-*a* of the ring may also be configured to receive updates (e.g., software/firmware updates) and data from the user device 106.

The wearable device 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the wearable device 104 may include a power source other than the battery 210, such as a capacitor. The power source (e.g., battery 210 or capacitor) may have a curved geometry that matches the curve of the wearable device 104. In some aspects, a charger or other power source may include additional sensors that may be used to collect data in addition to, or that supplements, data collected by the wearable device 104 itself. Moreover, a charger or other power source for the wearable device 104 may function as a user device 106, in which case the charger or other power source for the wearable device 104 may be configured to receive data from the wearable device 104, store and/or process data received from the wearable device 104, and communicate data between the wearable device 104 and the servers 110.

In some aspects, the wearable device 104 includes a power module 225 that may control charging of the battery 210. For example, the power module 225 may interface with an external wireless charger that charges the battery 210 when interfaced with the wearable device 104. The charger may include a datum structure that mates with a wearable device 104 datum structure to create a specified orientation with the wearable device 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage wearable device 104 charging, and under voltage wearable device 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the wearable device 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the wearable device 104 configured to contact the user's finger may have thermally conductive portions and thermally insulative portions. The thermally conductive portions may conduct heat from the user's finger to the temperature sensors 240. The thermally insulative portions may insulate portions of the wearable device 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the wearable device 104 may filter/reject temperature readings, such as large spikes in temperature that are not indicative of physiological changes (e.g., a temperature spike from a hot shower). In some implementations, the wearable device 104 may filter/reject temperature readings that may not be reliable due to other factors, such as excessive motion wearable device 104 exercise (e.g., as indicated by a motion sensor 245).

The wearable device 104 (e.g., communication module) may transmit the sampled and/or average temperature data to the user device 106 for storage and/or further processing. The user device 106 may transfer the sampled and/or average temperature data to the server 110 for storage and/or further processing.

Although the wearable device 104 is illustrated as including a single temperature sensor 240, the wearable device 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230-*a* may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the wearable device 104 may acquire distal temperatures at the user's finger (e.g., any finger). For example, one or more temperature sensors 240 on the wearable device 104 may acquire a user's temperature from the underside of a finger or at a different location on the finger. In some implementations, the wearable device 104 may continuously acquire distal temperature (e.g., at a sampling rate). Although distal temperature measured by a wearable device 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the wearable device 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The wearable device 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the wearable device 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The wearable device 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the wearable device 104 may include one or more accelerometers that generate acceleration signals that indicate acceleration of the accelerometers. As another example, the wearable device 104 may include one or more gyro sensors that generate gyro signals that indicate angular motion (e.g., angular velocity)

and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the wearable device 104 based on the sampled motion signals. For example, the processing module 230-*a* may sample acceleration signals to determine acceleration of the wearable device 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The wearable device 104 may store a variety of data described herein. For example, the wearable device 104 may store temperature data, such as raw sampled temperature data and calculated temperature data (e.g., average temperatures). As another example, the wearable device 104 may store PPG signal data, such as pulse waveforms and data calculated based on the pulse waveforms (e.g., heart rate values, IBI values, HRV values, and respiratory rate values). The wearable device 104 may also store motion data, such as sampled motion data that indicates linear and angular motion.

The wearable device 104, or other computing device, may calculate and store additional values based on the sampled/calculated physiological data. For example, the processing module 230-*a* may calculate and store various metrics, such as sleep metrics (e.g., a Sleep Score), activity metrics, and readiness metrics. In some implementations, additional values/metrics may be referred to as "derived values." The wearable device 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the wearable device 104 is oriented on the user's finger and if the wearable device 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the wearable device 104 last transmitted the data to the user device 106.

Although a user's physiological parameters may be measured by sensors included on a wearable device 104, other devices may measure a user's physiological parameters. For example, although a user's temperature may be measured by a temperature sensor 240 included in a wearable device 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken wearable device 104 portions of the day and/or portions of the night. In some implementations, the physiological measurements may be taken in response to determining that the user is in a specific state, such as an active state, resting state, and/or a sleeping state. For example, the wearable device 104 can make physiological measurements in a resting/sleep state in order to acquire cleaner physiological signals. In one example, the wearable device 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the wearable device 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the wearable device 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the wearable device 104, the user device 106, the servers 110, or any combination thereof. For example, in some cases, data collected by the wearable device 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the wearable device 104, user device 106, and server 110 of the system 200 may be configured to evaluate sleep patterns for a user. In particular, the respective components of the system 200 may be used to collect data from a user via the wearable device 104, and generate one or more scores (e.g., Sleep Score, Readiness Score) for the user based on the collected data. For example, as noted previously herein, the wearable device 104 of the system 200 may be worn by a user to collect data from the user, including temperature, heart rate, HRV, and the like. Data collected by the wearable device 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the wearable device 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some examples, a communication component (e.g., the communication module 220-a) may be coupled with an antenna. The antenna may be disposed along a first circumferential portion (e.g., an outer circumferential portion) of the wearable device 104 so that the antenna is separated from an antenna ground plane that is disposed along a second circumferential portion (e.g., an inner circumferential portion) of the wearable device 104. Such placement of the antenna may allow the antenna to be larger in size, and farther from an antenna ground plane, than other designs, which may improve the performance of the antenna relative to other designs, among other advantages. To prevent electrostatic charge on the antenna from damaging the communication component, an interconnect portion of the antenna that is coupled with an input of the communication component may be coupled with the antenna ground plane.

Figure 3:
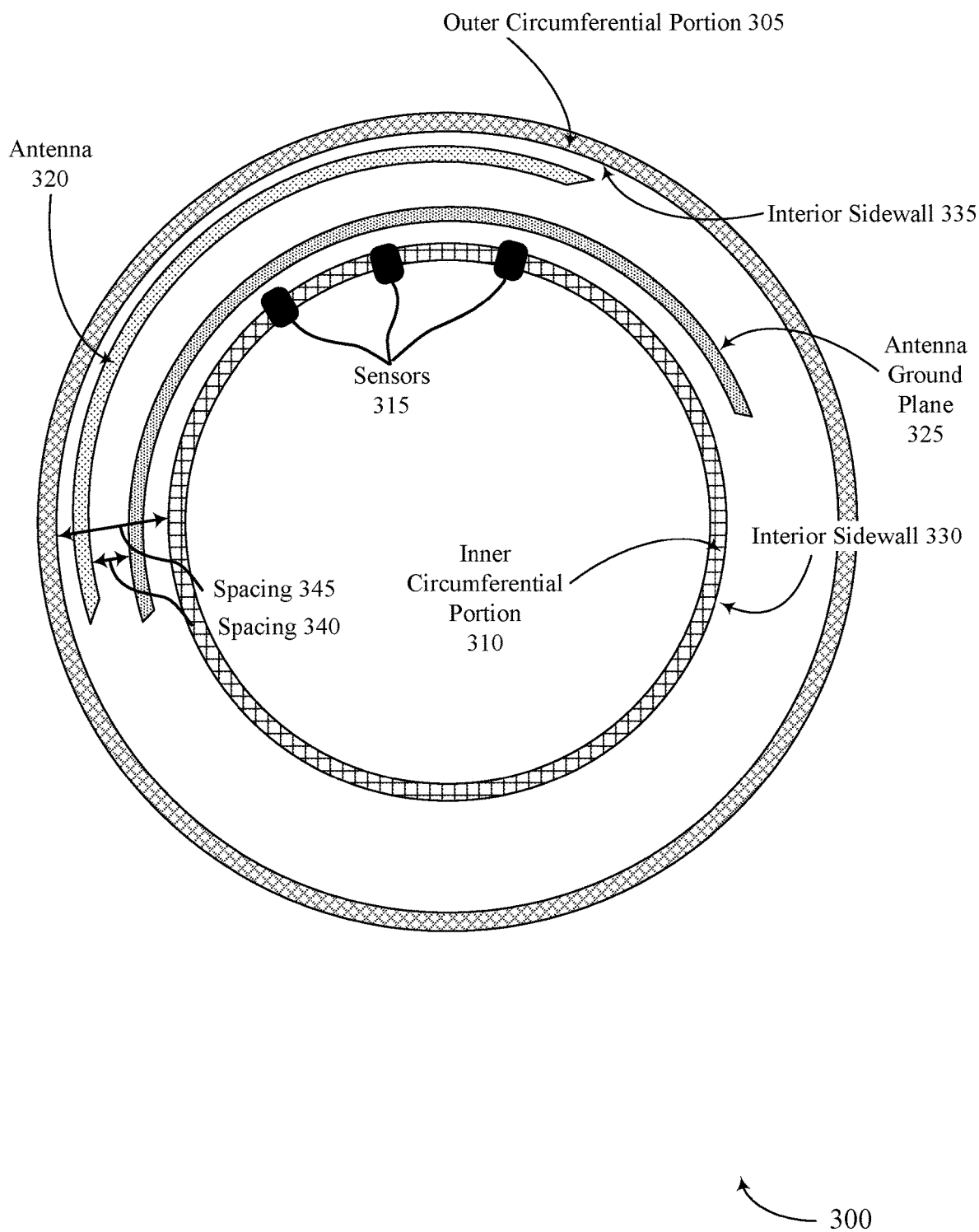
FIG. 3 illustrates an example of a wearable device that supports an antenna in accordance with aspects of the present disclosure.

FIG. 3 illustrates an example of a wearable device 300 that supports an antenna in accordance with aspects of the present disclosure. The wearable device 300 may be a wearable ring device and may include an outer circumferential portion 305 and an inner circumferential portion 310. The wearable device 300 may also include one or more sensor(s) 315 that extend through the inner circumferential portion and that are configured to sense physiological data for a user by interfacing with a user's skin. The sensors 315 may be coupled with a circuit board (e.g., a flexible printed circuit board) and may exchange signals with the circuit board. Although described with reference to a wearable ring device with circumferential portions, the designs described herein may be implemented in other types of wearable devices (e.g., wearable watch devices, wearable ankle devices), that have outer portions that are opposite inner portions (which may be configured to interface with the user's skin), regardless of the curvature of the portions.

The wearable device 300 may include an antenna 320 and an antenna ground plane 325, which may be a conductive (e.g., metal) material. Together, the antenna 320 and the antenna ground plane 325 may generate an electromagnetic field that the wearable device 300 can use for wireless communications with another device. For example, the antenna ground plane 325 may be configured to reflect an electromagnetic field that is generated by the antenna when the antenna is energized.

The antenna ground plane 325 may be disposed along the inner circumferential portion 310. For example, the antenna ground plane 325 may be curved and extend along the curvature of the interior sidewall 330 of the inner circumferential portion 310. The interior sidewall 330 may also be referred to as an inner surface, inner sidewall, interior surface, or other suitable terminology. The antenna ground plane may be the ground plane of a circuit board that is within the wearable device 300, may be an inner metal surface (e.g., a metal chassis) within the wearable device 300, or functionally speaking, may be considered to be both.

The antenna 320 may be disposed along the outer circumferential portion 305. For example, the antenna 320 may be curved and extend along the curvature of the interior sidewall 335 of the outer circumferential portion 305. The interior sidewall 335 may also be referred to as an inner surface, interior sidewall, interior surface, or other suitable terminology. In some examples, the antenna 320 may be a planar antenna. The antenna 320 may overlap with the antenna ground plane 325 so that an electromagnetic field can be generated between the antenna 320 and the antenna ground plane 325.

The antenna 320 may be placed along the interior sidewall 335 so that there is a spacing 340 between the antenna 320 and the antenna ground plane 325. The spacing 340 may be less than a spacing 345 between the inner circumferential portion 310 and the outer circumferential portion 305. By placing the antenna 320 along the interior sidewall 335, the spacing 340 may be increased relative to other designs, which may improve the performance (e.g., range, efficiency, bandwidth) of the antenna 320. Placing the antenna 320 along the interior sidewall 335 may also allow for a larger antenna 320 (e.g., more surface area for the radiator of the antenna 320), which may also increase the performance (e.g., range, efficiency, bandwidth) of the antenna relative to other designs.

In the illustrated example, the antenna ground plane 325 is disposed along the inner circumferential portion 310 and the antenna 320 is disposed along the outer circumferential portion 305. However, the positions of the antenna ground plane 325 and the antenna 320 may be switched so that the antenna ground plane 325 is disposed along the outer circumferential portion 305 and the antenna 320 is disposed along the inner circumferential portion 310. For example, the antenna ground plane 325 may be curved and extend along the curvature of the interior sidewall 335 and the antenna 320 may be curved and extend along the curvature of the interior sidewall 330. Placing the antenna 320 along the circumferential portion opposite the antenna ground plane 325 may increase the size of the antenna 320, and the spacing 340, relative to other designs, which in turn may improve the performance of the antenna 320.

Figure 4:
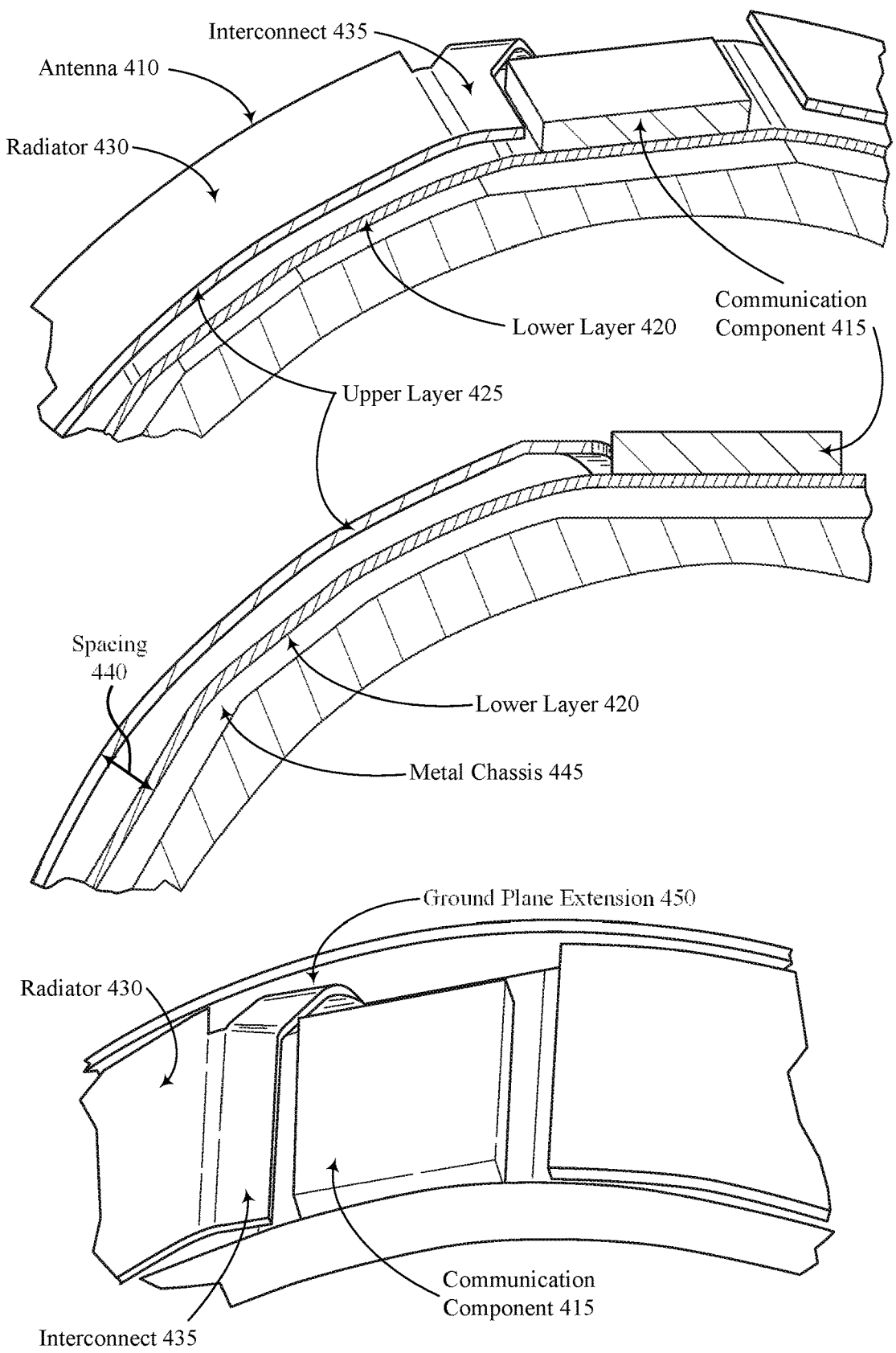
FIG. 4 illustrates an example of a wearable device that supports an antenna in accordance with aspects of the present disclosure.

FIG. 4 illustrates different views of a wearable device 400 that supports an antenna in accordance with aspects of the present disclosure. The wearable device 400 may be an example of a wearable device 104, a wearable device 104, or a wearable device 300 as described herein. The wearable device 400 may be configured to collect physiological data from a user and may include an antenna 410, a communication component 415, and a circuit board with a lower layer 420 and an upper layer 425.

The circuit board may be an example of a flexible printed circuit board and may include a lower layer 420 and an upper layer 425. The lower layer 420 may include a ground plane that acts as the antenna ground plane for the antenna 410 and that is disposed along the inner circumferential portion of the wearable device 400. The lower layer 420 may be adjacent to a metal surface (e.g., a metal chassis 445) that also extends along the inner circumferential portion of the wearable device 400. The upper layer 425 may be disposed along an outer circumferential portion of the wearable device 400 and may be configured to support the antenna 410.

The antenna 410 may be coupled with the upper layer 425 of the circuit board (e.g., a bottom surface of the antenna 410 may be coupled with a top surface of the upper layer 425) and may be disposed along the outer circumferential portion of the wearable device 400. The antenna 410 may include a radiator portion (e.g., radiator 430) that is configured to radiate an electromagnetic field and may include an interconnect portion (e.g., interconnect 435) that is configured to couple with an input of the communication component 415. In some examples, the radiator 430 may be a copper surface that is disposed on one or more metal layers of the upper layer 425.

By disposing the lower layer 420 along the inner circumferential portion of the wearable device 400 and disposing the upper layer 425 (with the antenna 410) along the outer circumferential portion of the wearable device, a spacing 440 may be created between the antenna 410 and the antenna ground plane (e.g., the ground plane of the lower layer 420, the metal chassis 445). The spacing 440 may be an example of the spacing 340 as described with reference to FIG. 3. As noted, increasing the size of the spacing 440 may improve the performance of the antenna 410. Further, disposing the antenna 410 along the outer circumferential portion of the wearable device 400 may increase the surface area of the radiator 430 relative to other designs, which in turn may improve the performance of the antenna 410.

In some examples, an air gap with spacing 440 may separate antenna 410 and the antenna ground plane. Alternatively, an insulative material with a low loss tangent, such as an epoxy, may separate the antenna 410 from the antenna ground plane. Use of an insulative material with low loss tangent, such as the epoxy, may improve antenna performance relative to other materials (e.g., polyurethane) with high loss tangents. In some examples, distributed portions of a material (e.g., an insulative material with a low loss tangent) may be used to maintain the spacing 440 between the antenna 410 and the antenna ground plane. In such examples, the spaces between the portions of material may be filled with air (e.g., the portions of material may be separated by air gaps so that the portions are isolated from each other), which may improve antenna performance compared to designs that use the material without air gaps.

The communication component 415 may be configured to wirelessly communicate with other devices using the antenna 410. For example, the communication component 415 may be configured to energize the antenna 410 so that the antenna 410 generates an electromagnetic field. In some examples, the communication component 415 may be a Bluetooth component. However, other types of communication components are contemplated and within the scope of the present disclosure.

The communication component 415 may interface with the antenna 410 via an input that is coupled with the interconnect 435. To prevent electrostatic discharge on the radiator 430 from damaging the communication component 415, the interconnect 435 may be coupled with the antenna ground plane via a portion of the circuit board (e.g., ground plane extension 450) that couples the lower layer 420 with the upper layer 425. Coupling the interconnect 435 with the antenna ground plane may provide a lower resistance path for electrical signals compared to the input of the communication component 415. Thus, both the radiator 430 and the interconnect 435 may be configured to conduct electrostatic discharge to the antenna ground plane (and away from the input), which may prevent the communication component 415 from being damaged. Coupling the antenna ground plane to the interconnect 435 (as opposed the radiator 430) may ensure that any electrostatic discharge on the radiator 430 is conducted to the antenna ground plane, regardless of where the electrostatic discharge hits the radiator 430.

Although shown with the lower layer 420 disposed along the inner circumferential portion of the wearable device 400 and the upper layer 425 (with the antenna 410) disposed along the outer circumferential portion of the wearable device 400, in some configurations the positioning of the lower layer 420 and the upper layer 425 may be switched. For example, in an alternative design the lower layer 420 may be disposed along the outer circumferential portion of the wearable device 400 and the upper layer 425 (with the antenna 410) may be disposed along the inner circumferential portion of the wearable device 400.

Thus, the performance of the antenna 410 may be increased relative to other designs by disposing the antenna 410 along the circumferential portion of the wearable device 400 that is opposite the circumferential portion along which the antenna ground plane is disposed.

Figure 5:
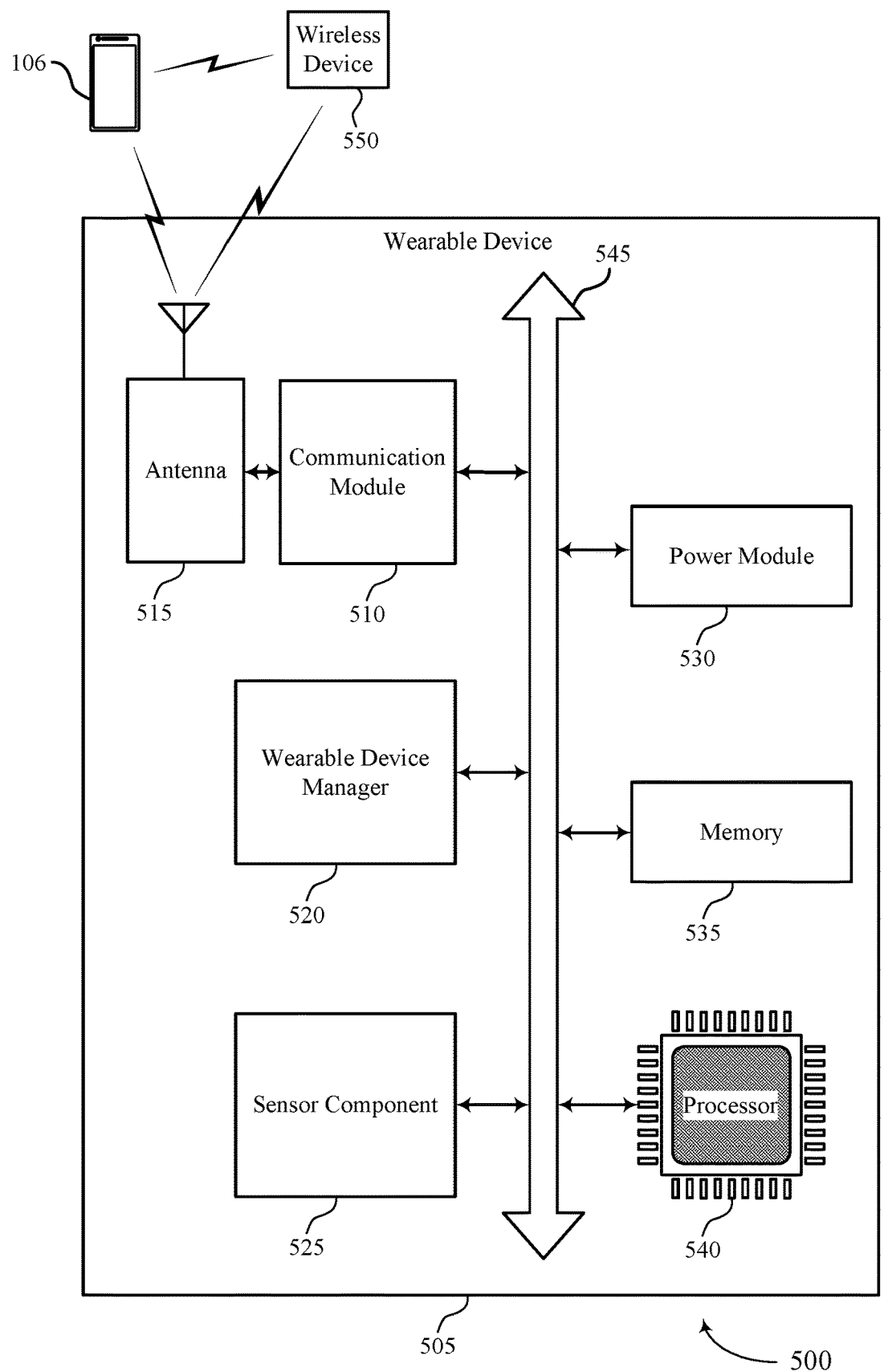
FIG. 5 shows a diagram of a system including a device that supports an antenna in accordance with aspects of the present disclosure.

FIG. 5 shows a diagram of a system 500 including a device 505 that supports an antenna in a wearable device in accordance with aspects of the present disclosure. The device 505 may include an example of a wearable device 104, as described previously herein. The device 505 may include components for bi-directional communications including components for transmitting and receiving communications with a user device 106 and a server 110, such as a wearable device manager 520, a communication module 510, an antenna 515, a sensor component 525, a power module 530, a memory 535, a processor 540, and a wireless device 550. These components may be in electronic communication or otherwise coupled (e.g., operatively, communicatively, functionally, electronically, electrically) via one or more buses (e.g., a bus 545).

The antenna 515 may be an example of an antenna 320 or an antenna 410 as described with reference to FIGS. 3 and 4, respectively. The communication module 510 may be an example of a communication component 415 as described with reference to FIG. 4. The antenna 515 may be configured as described herein (e.g., disposed along a first circumferential portion of the device 505 that is opposite a second circumferential portion along which an antenna ground plane is disposed), and thus may have improved performance relative to other configurations.

The wearable device manager 520 may be configured as or otherwise support a means for performing the operations described herein.

It should be noted that the methods described above describe possible implementations, and that the operations and the steps may be rearranged or otherwise modified and that other implementations are possible. Furthermore, aspects from two or more of the methods may be combined.

A wearable device (e.g., a wearable ring device) is described. The wearable device may include a first circumferential portion and a second circumferential portion separated by a first spacing, an antenna ground plane within the wearable device and disposed along the first circumferential portion, and an antenna within the wearable device and disposed along the second circumferential portion and separated from the antenna ground plane by a second spacing less than the first spacing, the antenna comprising an interconnect portion that couples a radiator of the antenna with the antenna ground plane at an input of a communication component for the antenna, wherein the interconnect portion is configured to conduct electrostatic discharge on the radiator away from the communication component and toward the antenna ground plane.

In some examples, the first circumferential portion comprises an inner circumferential portion that may be configured to interface with the skin of a user and the second circumferential portion comprises an outer circumferential portion that may be opposite the inner circumferential portion. In some examples, the first circumferential portion comprises an outer circumferential portion and the second circumferential portion comprises an inner circumferential portion that may be opposite the outer circumferential portion and that may be configured to interface with the skin of a user.

In some examples, the antenna may be separated from the antenna ground plane by an air gap. In some examples, the antenna may be separated from the antenna ground plane by an insulative material. In some examples, the insulative material comprises an epoxy. In some examples, portions of insulative material between the antenna ground plane and the antenna and configured to maintain the second spacing between the antenna ground plane and the antenna, the portions of insulative material separated by air gaps.

In some examples, the antenna and the antenna ground plane may be configured to generate an electromagnetic field for wireless communication and a range of the electromagnetic field may be based at least in part on the second spacing. In some examples, a metal surface curved along an interior sidewall of the first circumferential portion, wherein the antenna ground plane comprises the metal surface.

In some examples, the antenna comprises a planar antenna that may be curved along an interior sidewall of the second circumferential portion. In some examples, a flexible printed circuit board within the wearable device, wherein the antenna ground plane comprises a ground plane of the flexible printed circuit board. In some examples, the flexible printed circuit board may be curved along an interior sidewall of the first circumferential portion.

In some examples, the flexible printed circuit board may include operations, features, means, or instructions for an upper layer upon which the antenna may be disposed and a lower layer that comprises the ground plane and that may be disposed between the first circumferential portion and the upper layer. In some examples, the communication component may be disposed on the lower layer and the input of the communication component may be coupled with the upper layer. In some examples, wearable device may include a sensor coupled with the flexible printed circuit board and extending through the first circumferential portion, the sensor configured to sense physiological data for a user of the wearable device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device, comprising:
   a first circumferential portion and a second circumferential portion separated by a first spacing;
   an antenna ground plane within the wearable ring device and disposed along the first circumferential portion;
   an antenna within the wearable ring device and disposed along the second circumferential portion and separated from the antenna ground plane by a second spacing less than the first spacing, the antenna comprising an interconnect portion that couples a radiator of the antenna with the antenna ground plane at an input of a communication component for the antenna; and
   a ground plane extension, of a circuit board, that spans the second spacing and that extends from an upper layer of the circuit board that comprises the radiator to a lower layer of the circuit board that comprises the antenna ground plane, wherein the interconnect portion is configured to conduct electrostatic discharge on the radiator away from the communication component and toward the antenna ground plane via the ground plane extension.

2. The wearable ring device of claim 1, wherein the first circumferential portion comprises an inner circumferential portion that is configured to interface with the skin of a user, and wherein the second circumferential portion comprises an outer circumferential portion that is opposite the inner circumferential portion.

3. The wearable ring device of claim 1, wherein the first circumferential portion comprises an outer circumferential portion, and wherein the second circumferential portion comprises an inner circumferential portion that is opposite the outer circumferential portion and that is configured to interface with the skin of a user.

4. The wearable ring device of claim 1, wherein the antenna is separated from the antenna ground plane by an air gap.

5. The wearable ring device of claim 1, wherein the antenna is separated from the antenna ground plane by an insulative material.

6. The wearable ring device of claim 5, wherein the insulative material comprises an epoxy.

7. The wearable ring device of claim 1, further comprising:
   portions of insulative material between the antenna ground plane and the antenna and configured to maintain the second spacing between the antenna ground plane and the antenna, the portions of insulative material separated by air gaps.

8. The wearable ring device of claim 1, wherein the antenna and the antenna ground plane are configured to generate an electromagnetic field for wireless communication, and a range of the electromagnetic field is based at least in part on the second spacing.

9. The wearable ring device of claim 1, further comprising:
   a metal surface curved along an interior sidewall of the first circumferential portion, wherein the antenna ground plane comprises the metal surface.

10. The wearable ring device of claim 1, wherein the antenna comprises a planar antenna that is curved along an interior sidewall of the second circumferential portion.

11. The wearable ring device of claim 1, wherein the circuit board comprises a flexible printed circuit board within the wearable ring device, wherein the antenna ground plane comprises a ground plane of the flexible printed circuit board.

12. The wearable ring device of claim 11, wherein the flexible printed circuit board is curved along an interior sidewall of the first circumferential portion.

13. The wearable ring device of claim 1, wherein the communication component is disposed on the lower layer and the input of the communication component is coupled with the upper layer.

14. The wearable ring device of claim 11, wherein the first circumferential portion comprises an inner circumferential portion, the wearable ring device further comprising:
   a sensor coupled with the flexible printed circuit board and extending through the first circumferential portion, the sensor configured to sense physiological data for a user of the wearable ring device.

* * * * *